(12) United States Patent
Johanson et al.

(10) Patent No.: US 7,442,526 B2
(45) Date of Patent: Oct. 28, 2008

(54) METHOD FOR PREPARING A PHYSIOLOGICALLY ACTIVE IL-18 POLYPEPTIDE

(75) Inventors: Kyung O. Johanson, King of Prussia, PA (US); Robert B. Kirkpatrick, King of Prussia, PA (US); Allan R. Shatzman, King of Prussia, PA (US); Yen Sen Ho, Berwyn, PA (US); Patrick McDevitt, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 11/402,187

(22) Filed: Apr. 11, 2006

(65) Prior Publication Data

US 2006/0177422 A1    Aug. 10, 2006

Related U.S. Application Data

(62) Division of application No. 10/311,491, filed as application No. PCT/US01/18804 on Jun. 11, 2001, now Pat. No. 7,186,528.

(60) Provisional application No. 60/211,832, filed on Jun. 15, 2000, provisional application No. 60/224,128, filed on Aug. 10, 2000, provisional application No. 60/264,923, filed on Jan. 30, 2001.

(51) Int. Cl.
    *C12P 21/02* (2006.01)
(52) U.S. Cl. ............... 435/69.7; 435/69.52; 530/351
(58) Field of Classification Search .................. None
    See application file for complete search history.

(56) References Cited

U.S. PATENT DOCUMENTS

| | | | |
|---|---|---|---|
| 5,914,254 A | 6/1999 | Mascarenhas et al. | 435/69.7 |
| 5,985,863 A | 11/1999 | Su et al. | 514/183 |
| 6,054,487 A | 4/2000 | Sekut et al. | 514/604 |

FOREIGN PATENT DOCUMENTS

EP          0921005         1/1998

OTHER PUBLICATIONS

Sequence search results: sequence alignment between SEQ ID No. 4 of the present application and the sequence of Figure 1A of Munday et al., J. Biol. Chem., 1995, 270(26):15870-76.*
Fassay, et al., "Enzymatic Activity of Two Caspases Related to Interleukin-1beta-Converting Enzyme," *Eur. J. Biochem.*, 253(1): 76-83 (1998).
Garcia-Calvo, et al., "Purification and Catalytic Properties of Human Caspase Family Members," *Cell Death and Diff.*, 6(4): 362-369 (1999).
Ghayur, et al., "Caspase-1 Processes IFN-Gamma-Inducing Factor and Regulates LPS-Induced IFN-Gamma Production," *Nature*, 389: 619-623 (1997).
Munday, et al., "Molecular Cloning and Pro-Apoptotic Activity of ICErelII and ICErelIII, Memebers of the ICE/CED-3 Family of Cysteine Proteases," *J. Biol. Chem.*, 270: 15870-15876 (1995).
Ushio, et al., "Cloning of the cDNA for Human IFN-Gamma-Inducing Factor, Expression in *Escherichia coli*, and Studies on the Biologic Activities of the Protein," *J. Immunol.*, 156: 4274-4279 (1996).
Howard, et al., "Human IL-1-beta Processing and Secretion in Recombinant Baculovirus-Infected Sf9 Cells is Blocked by the Cowpox Virus Serpin crmA," *Journal of Immunology*, 154(5), pp. 2321-2332, (1995).
Hsieh, et al., "Improved Gene Expression by a Modified Bicistronic Retroviral Vector," *Biochemical and Biophysical Research Communications*, 214(3), pp. 910-917, (1995).
Muneta, et al., "Efficient Production of Biologically Active Porcine Interleukin-18 by Coexpression with Porcine Caspase-1 Using a Baculovirus Expression System," *Journal of Interferon and Cytokine Research*, 21(2), pp. 125-130, (2001).
Hildinger, et al., "Bicistronic Retroviral Vectors for Combining Myeloprotection with Cell-surface Marking," *Gene Therapy*, 6(7), pp. 1222-1230, (1999).
Harris, et al., "A New Baculovirus Expression Vector for the Simultaneous Expression of Two Heterologous Proteins in the Same Insect Cell," *Focus*, 19(1), pp. 10-12, (1996).
Dang, et al., "Preparation of an Autolysis-resistant IL-1b Converting Enzyme Mutant," *Biochemistry*, 35:149, pp. 14910-14916, (1996).

* cited by examiner

*Primary Examiner*—Dong Jiang
(74) *Attorney, Agent, or Firm*—Elizabeth J. Hecht; Edward R. Gimmi; Sherry M. Knowles

(57) ABSTRACT

The present invention provides a method for producing physiologically active human Interleukin-18 ("IL-18").

1 Claim, 7 Drawing Sheets

FIGURE 1

T7 ➜ RBS Pro IL18 RBS Casp4

FIGURE 3

T7 ➔ RBS Pro IL18 RBS Casp5

1. Ub-human IL18, 3 hours
2. Ub-human IL18/Ubp-1, O hours
3. Ub-human IL18/Ubp-1, 3 hours
4. Ub-human IL18/Ubp-1, 18 hours C. Control- ProIL18/Casp 4

Western: Anti IL18

FIGURE 6

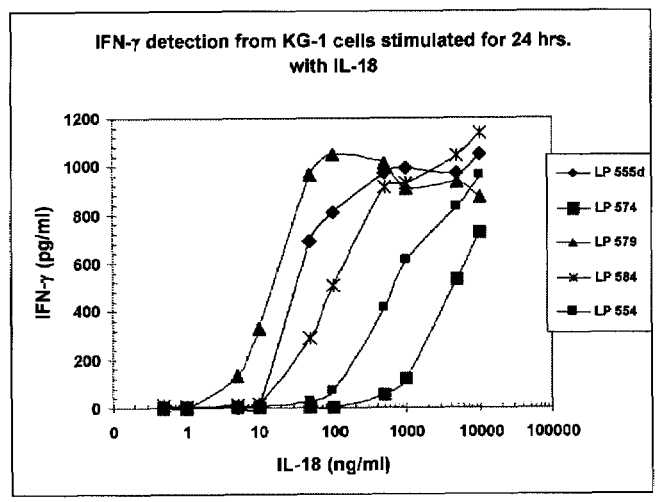

Description of different human/murine IL-18 samples (different lots/constructs)

| |
|---|
| LP555d (standard) E. COLI ICE-CLEAVED (*IN VITRO*) |
| LP 554 E. coli murine IL-18 Ice-cleaved (*IN VITRO*) |
| LP559 E. coli expressed mature IL-18 containing N-terminal methionine |
| LP574 E. coli expressed mature IL-18 containing N-terminal Methionine |
| LP579 Pichia expressed, secreted, mature IL18 |
| LP584 E.coli IL-18/ICE bicistronic co-expression (*IN VIVO*) |
| LP594 E. coli ICE-cleaved (*IN VITRO*) |
| LP613 E. coli caspase 4 cleaved (*IN VITRO*) |
| LP614 E. coli ICE co-expressed (*IN VITRO*) |
| LP623 caspase 4 co-expressed (*IN VIVO*) |

FIGURE 7

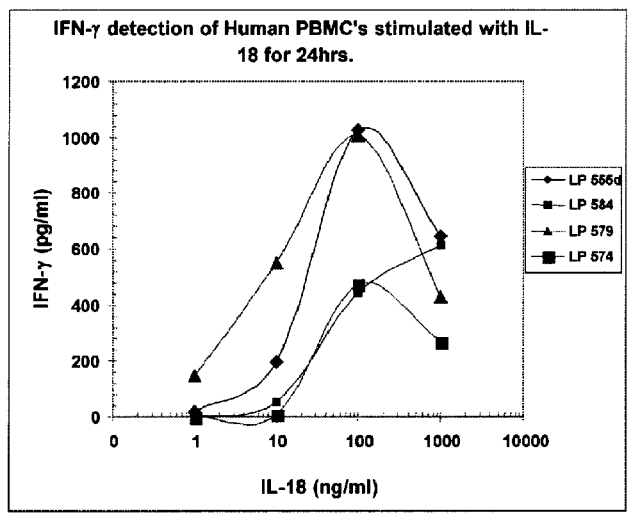

Description of different human/murine IL-18 samples (different lots/constructs)

| |
|---|
| LP555d (standard) E. COLI ICE-CLEAVED (*IN VITRO*) |
| LP 554 E. coli murine IL-18 Ice-cleaved (*IN VITRO*) |
| LP559 E. coli expressed mature IL-18 containing N-terminal methionine |
| LP574 E. coli expressed mature IL-18 containing N-terminal Methionine |
| LP579 Pichia expressed, secreted, mature IL18 |
| LP584 E.coli IL-18/ICE bicistronic co-expression (*IN VIVO*) |
| LP594 E. coli ICE-cleaved (*IN VITRO*) |
| LP613 E. coli caspase 4 cleaved (*IN VITRO*) |
| LP614 E. coli ICE co-expressed (*IN VITRO*) |
| LP623 caspase 4 co-expressed (*IN VIVO*) |

```
                           SEQUENCE LISTING

<160> NUMBER OF SEQ ID NOS: 12

<210> SEQ ID NO 1
<211> LENGTH: 193
<212> TYPE: PRT
<213> ORGANISM: Homo sapien

<400> SEQUENCE: 1

Met Ala Ala Glu Pro Val Glu Asp Asn Cys Ile Asn Phe Val Ala Met
 1               5                  10                  15

Lys Phe Ile Asp Asn Thr Leu Tyr Phe Ile Ala Glu Asp Glu Asn
                20                  25                  30

Leu Glu Ser Asp Tyr Phe Gly Lys Leu Glu Ser Lys Leu Ser Val Ile
                35                  40                  45

Arg Asn Leu Asn Asp Gln Val Leu Phe Ile Asp Gln Gly Asn Arg Pro
    50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
                100                 105                 110

Glu Asn Lys Ile Ile Ser Phe Lys Glu Met Asn Pro Pro Asp Asn Ile
            115                 120                 125

Lys Asp Thr Lys Ser Asp Ile Ile Phe Phe Gln Arg Ser Val Pro Gly
        130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
                180                 185                 190

Asp

SEQ ID NO 2

<211> LENGTH: 582
<212> TYPE: DNA
<213> ORGANISM: Homo sapien

<400> SEQUENCE: 2
atggctgctg aaccagtaga agacaattgc atcaactttg tggcaatgaa atttattgac      60
aatacgcttt actttatagc tgaagatgat gaaaacctgg aatcagatta ctttggcaag     120
cttgagagca aactatcggt cattcgtaat ttaaatgacc aggtcctatt tatcgaccaa     180
gggaatcgtc cactattcga ggacatgaca gacagtgact gccgagacaa tgcgccgcga     240
accattttca ttatatctat gtacaaggat tctcagccgc gcggaatggc cgtaactatt     300
tctgtcaaat gtgaaaagat atccacgctg tcgtgtgaga acaagattat tagtttcaaa     360
gagatgaatc cgccggataa tatcaaggac acgaagtctg atatcatatt tttccagcgc     420
agcgtgccgg ggcacgataa caagatgcaa tttgaatcat ccagctatga agggtacttt     480
```

-continued

```
cttgcatgcg agaaggaacg cgatctcttt aaacttattt taaagaaaga ggacgagcta    540
ggcgatcgca gcattatgtt cactgtccaa aatgaagact ag                       582
```

```
<210> SEQ ID NO 3
<211> LENGTH: 157
<212> TYPE: PRT
<213> ORGANISM: Homo sapien

<400> SEQUENCE: 3

Tyr Phe Gly Lys Leu Glu Ser Lys Leu Ser Val Ile Arg Asn Leu Asn
 1               5                  10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
        50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Glu Asp Glu Leu
    130                 135                 140

Gly Asp Arg Ser Ile Met Phe Thr Val Gln Asn Glu Asp
145                 150                 155
```

```
<210> SEQ ID NO 4
<211> LENGTH: 282
<212> TYPE: PRT
<213> ORGANISM: Homo sapien

<400> SEQUENCE: 4

Met Gly His His His His His His Gly Ala Leu Lys Leu Cys Pro His
 1               5                  10                  15

Glu Glu Phe Leu Arg Leu Cys Lys Glu Arg Ala Glu Glu Ile Tyr Pro
                20                  25                  30

Ile Lys Glu Arg Asn Asn Arg Thr Arg Leu Ala Leu Ile Ile Cys Asn
            35                  40                  45

Thr Glu Phe Asp His Leu Pro Pro Arg Asn Gly Ala Asp Phe Asp Ile
        50                  55                  60

Thr Gly Met Lys Glu Leu Leu Glu Gly Leu Asp Tyr Ser Val Asp Val
65                  70                  75                  80

Glu Glu Asn Leu Thr Ala Arg Asp Met Glu Ser Ala Leu Arg Ala Phe
                85                  90                  95

Ala Thr Arg Pro Glu His Lys Ser Ser Asp Ser Thr Phe Leu Val Leu
            100                 105                 110

Met Ser His Gly Ile Leu Glu Gly Ile Cys Gly Thr Val His Asp Glu
        115                 120                 125

Lys Lys Pro Asp Val Leu Leu Tyr Asp Thr Ile Phe Gln Ile Phe Asn
    130                 135                 140

Asn Arg Asn Cys Leu Ser Leu Lys Asp Lys Pro Lys Val Ile Ile Val
```

```
                145                 150                 155                 160
Gln Ala Cys Arg Gly Ala Asn Arg Gly Glu Leu Trp Val Arg Asp Ser
                165                 170                 175

Pro Thr Ser Leu Glu Val Ala Ser Ser Gln Ser Ser Glu Asn Leu Glu
            180                 185                 190

Glu Asp Ala Val Tyr Lys Thr His Val Glu Lys Asp Phe Ile Ala Phe
            195                 200                 205

Cys Ser Ser Thr Pro His Asn Val Ser Trp Arg Asp Ser Thr Met Gly
        210                 215                 220

Ser Ile Phe Ile Thr Gln Leu Ile Thr Cys Phe Gln Lys Tyr Ser Trp
225                 230                 235                 240

Cys Cys His Leu Glu Glu Val Phe Arg Lys Val Gln Gln Ser Phe Glu
                245                 250                 255

Thr Pro Arg Ala Lys Ala Gln Met Pro Thr Ile Glu Arg Leu Ser Met
            260                 265                 270

Thr Arg Tyr Phe Tyr Leu Phe Pro Gly Asn
            275                 280

<210> SEQ ID NO 5
<211> LENGTH: 849
<212> TYPE: DNA
<213> ORGANISM: Homo sapien

<400> SEQUENCE: 5
atgggccatc atcatcatca tcatggcgcc ctcaagcttt gtcctcatga agaattcctg      60
agactatgta agaaagagc  tgaagagatc tatccaataa aggagagaaa caaccgcaca     120
cgcctggctc tcatcatatg caatacagag tttgaccatc tgcctccgag gaatggagct     180
gactttgaca tcacagggat gaaggagcta cttgagggtc tggactatag tgtagatgta     240
gaagagaatc tgcacagccag ggatatggag tcagcgctga gggcatttgc taccagacca    300
gagcacaagt cctctgacag cacattcttg gtactcatgt ctcatggcat cctggaggga    360
atctgcggaa ctgtgcatga tgagaaaaaa ccagatgtgc tgctttatga caccatcttc    420
cagatattca acaaccgcaa ctgcctcagt ctgaaggaca aacccaaggt catcattgtc    480
caggcctgca gaggtgcaaa ccgtggggaa ctgtgggtca gagactctcc agcatccttg    540
gaagtggcct cttcacagtc atctgagaac ctggaggaag atgctgttta caagacccac    600
gtggagaagg acttcattgc tttctgctct tcaacgccac acaacgtgtc ctggagagac    660
agcacaatgg gctctatctt catcacacaa ctcatcacat gcttccagaa atattcttgg    720
tgctgccacc tagaggaagt atttcggaag gtacagcaat catttgaaac tccaagggcc    780
aaagctcaaa tgcccaccat agaacgactg tccatgacaa gatatttcta cctctttcct    840
ggcaattga                                                             849

<210> SEQ ID NO 6
<211> LENGTH: 282
<212> TYPE: PRT
<213> ORGANISM: Homo sapien

<400> SEQUENCE: 6

Met Gly His His His His His His Gly Ile Leu Lys Leu Cys Pro Arg
1               5                   10                  15

Glu Glu Phe Leu Arg Leu Cys Lys Lys Asn His Asp Glu Ile Tyr Pro
            20                  25                  30

Ile Lys Lys Arg Glu Asp Arg Arg Arg Leu Ala Leu Ile Ile Cys Asn
```

```
                  35                  40                  45
Thr Lys Phe Asp His Leu Pro Ala Arg Asn Gly Ala His Tyr Asp Ile
 50                  55                  60

Val Gly Met Lys Arg Leu Leu Gln Gly Leu Gly Tyr Thr Val Val Asp
 65                  70                  75                  80

Glu Lys Asn Leu Thr Ala Arg Asp Met Glu Ser Val Leu Arg Ala Phe
                 85                  90                  95

Ala Ala Arg Pro Glu His Lys Ser Ser Asp Ser Thr Phe Leu Val Leu
            100                 105                 110

Met Ser His Gly Ile Leu Glu Gly Ile Cys Gly Thr Ala His Lys Lys
        115                 120                 125

Lys Lys Pro Asp Val Leu Leu Tyr Asp Thr Ile Phe Gln Ile Phe Asn
130                 135                 140

Asn Arg Asn Cys Leu Ser Leu Lys Asp Lys Pro Lys Val Ile Ile Val
145                 150                 155                 160

Gln Ala Cys Arg Gly Glu Lys His Gly Glu Leu Trp Val Arg Asp Ser
                165                 170                 175

Pro Ala Ser Leu Ala Val Ile Ser Ser Gln Ser Ser Glu Asn Leu Glu
            180                 185                 190

Ala Asp Ser Val Cys Lys Ile His Glu Glu Lys Asp Phe Ile Ala Phe
        195                 200                 205

Cys Ser Ser Thr Pro His Asn Val Ser Trp Arg Asp Arg Thr Arg Gly
210                 215                 220

Ser Ile Phe Ile Thr Glu Leu Ile Thr Cys Phe Gln Lys Tyr Ser Cys
225                 230                 235                 240

Cys Cys His Leu Met Glu Ile Phe Arg Lys Val Gln Lys Ser Phe Glu
                245                 250                 255

Val Pro Gln Ala Lys Ala Gln Met Pro Thr Ile Glu Arg Ala Thr Leu
            260                 265                 270

Thr Arg Asp Phe Tyr Leu Phe Pro Gly Asn
        275                 280
```

<210> SEQ ID NO 7
<211> LENGTH: 849
<212> TYPE: DNA
<213> ORGANISM: Homo sapien

<400> SEQUENCE: 7

```
atgggccatc atcatcatca tcatggcata ctcaaacttt gtcctcgtga agaattcctg    60
agactgtgta aaaaaaatca tgatgagatc tatccaataa aaagagaga ggaccgcaga   120
cgcctggctc tcatatatg caatacaaag tttgatcacc tgcctgcaag gaatgggct    180
cactatgaca tcgtgggat gaaaaggctg cttcaaggcc tgggctacac tgtggttgac   240
gaaaagaatc tcacagccag ggatatggag tcagtgctga ggcatttgc tgccagacca   300
gagcacaagt cctctgacag cacgttcttg gtactcatgt ctcatggcat cctagaggga   360
atctgcggaa ctgcgcataa aagaaaaaa ccggatgtgc tgctttatga caccatcttc   420
cagatattca caaccgcaa ctgcctcagt ctaaaggaca aacccaaggt catcattgtc   480
caggcctgca gaggtgaaaa acatggggaa ctctgggtca gagactctcc agcatccttg   540
gcagtcatct cttcacagtc atctgagaac ctggaggcag attctgtttg caagatccac   600
gaggagaagg acttcattgc tttctgttct tcaacaccac ataacgtgtc ctggagagac   660
cgcacaaggg gctccatctt cattacggaa ctcatcacat gcttccagaa atattcttgc   720
```

```
tgctgccacc taatggaaat atttcggaag gtacagaaat catttgaagt tccacaggct      780
aaagcccaga tgcccaccat agaacgagca accttgacaa gagatttcta cctctttcct      840
ggcaattga                                                              849
```

<210> SEQ ID NO 8
<211> LENGTH: 1743
<212> TYPE: DNA
<213> ORGANISM: Homo sapien

<400> SEQUENCE: 8

```
agatctcgat cccgcgaaat taatacgact cactataggg gaattgtgag cggataacaa       60
ttcccctcta gaccacacct taaggaggat ataacatatg gctgctgaac cagtagaaga      120
caattgcatc aactttgtgg caatgaaatt tattgacaat acgctttact ttatagctga      180
agatgatgaa aacctggaat cagattactt tggcaagctt gagagcaaac tatcggtcat      240
tcgtaattta aatgaccagg tcctatttat cgaccaaggg aatcgtccac tattcgagga      300
catgacagac agtgactgcc gagacaatgc gccgcgaacc attttcatta tatctatgta      360
caaggattct cagccgcgcg gaatggccgt aactatttct gtcaaatgtg aaagatatc       420 cacgctgtcg tgtgagaaca agattattag tttcaaagag atgaatccgc cggataatat      480
caaggacacg aagtctgata tcatattttt ccagcgcagc gtgccggggc acgataacaa      540
gatgcaattt gaatcatcca gctatgaagg gtactttctt gcatgcgaga aggaacgcga      600
tctctttaaa cttatttaa agaaagagga cgagctaggc gatcgcagca ttatgttcac       660
tgtccaaaat gaagactagt ggaggatata ataccaggaa taaataaaat ccatgggcca      720
tcatcatcat catcatggcg ccctcaagct ttgtcctcat gaagaattcc tgagactatg      780
taaagaaaga gctgaagaga tctatccaat aaaggagaga acaaccgca cacgcctggc       840 tctcatcata tgcaatacag agtttgacca tctgcctccg aggaatggag ctgactttga      900
catcacaggg atgaaggagc tacttgaggg tctggactat agtgtagatg tagaagagaa      960
tctgacagcc agggatatgg agtcagcgct gagggcattt gctaccagac cagagcacaa     1020
gtcctctgac agcacattct tggtactcat gtctcatggc atcctggagg gaatctgcgg     1080
aactgtgcat gatgagaaaa aaccagatgt gctgctttat gacaccatct tccagatatt     1140
caacaaccgc aactgcctca gtctgaagga caaacccaag gtcatcattg tccaggcctg     1200
cagaggtgca aaccgtgggg aactgtgggt cagagactct ccagcatcct tggaagtggc     1260
ctcttcacag tcatctgaga acctggagga agatgctgtt tacaagaccc acgtggaaaa     1320
ggacttcatt gctttctgct cttcaacgcc acacaacgtg tcctggagag acagcacaat     1380
gggctctatc ttcatcacac aactcatcac atgcttccag aaatattctt ggtgctgcca     1440
cctagaggaa gtatttcgga aggtacagca atcatttgaa actccaaggg ccaaagctca     1500
aatgcccacc atagaacgac tgtccatgac aagatatttc tacctctttc ctggcaattg     1560
aaaatggatc cgaattcgag ctccgtcgac aagcttgcgg ccgcactcga gcaccaccac     1620
caccaccact gagatccggc tgctaacaaa gcccgaaagg aagctgagtt ggctgctgcc     1680
accgctgagc aataactagc ataacccctt ggggcctcta acgggtctt gaggggtttt      1740 ttg                                                                   1743
```

<210> SEQ ID NO 9
<211> LENGTH: 1464
<212> TYPE: DNA
<213> ORGANISM: Homo sapien

<400> SEQUENCE: 9

```
atggctgctg aaccagtaga agacaattgc atcaactttg tggcaatgaa atttattgac      60
aatacgcttt actttatagc tgaagatgat gaaaacctgg aatcagatta ctttggcaag     120
cttgagagca aactatcggt cattcgtaat ttaaatgacc aggtcctatt tatcgaccaa     180
gggaatcgtc cactattcga ggacatgaca gacagtgact gccgagacaa tgcgccgcga     240
accattttca ttatatctat gtacaaggat tctcagccgc gcggaatggc cgtaactatt     300
tctgtcaaat gtgaaaagat atccacgctg tcgtgtgaga acaagattat tagtttcaaa     360
gagatgaatc cgccggataa tatcaaggac acgaagtctg atatcatatt tttccagcgc     420
agcgtgccgg ggcacgataa caagatgcaa tttgaatcat ccagctatga agggtacttt     480
cttgcatgcg agaaggaacg cgatctcttt aaacttattt taagaaaaga ggacgagcta     540
ggcgatcgca gcattatgtt cactgtccaa atgaagact agtggaggat ataataccag     600
gaataaataa aatccatggg ccatcatcat catcatcatg gcatactcaa actttgtcct     660
cgtgaagaat tcctgagact gtgtaaaaaa atcatgatg agatctatcc aataaaaaag      720
agagaggacc gcagacgcct ggctctcatc atatgcaata caaagtttga tcacctgcct     780
gcaaggaatg gggctcacta tgacatcgtg gggatgaaaa ggctgcttca aggcctgggc     840
tacactgtgg ttgacgaaaa gaatctcaca gccaggata tggagtcagt gctgagggca      900
tttgctgcca gaccagagca caagtcctct gacagcacgt tcttggtact catgtctcat     960
ggcatcctag agggaatctg cggaactgcg cataaaaaga aaaaaccgga tgtgctgctt    1020
tatgacacca tcttccagat attcaacaac gcaactgcc tcagtctaaa ggacaaaccc     1080
aaggtcatca ttgtccaggc ctgcagaggt gaaaaacatg gggaactctg gtcagagac     1140
tctccagcat ccttggcagt catctcttca cagtcatctg agaacctgga ggcagattct    1200
gtttgcaaga tccacgagga gaaggacttc attgctttct gttcttcaac accacataac    1260
gtgtcctgga gagaccgcac aaggggctcc atcttcatta cggaactcat cacatgcttc    1320
cagaaatatt cttgctgctg ccacctaatg gaaatatttc ggaaggtaca gaaatcattt    1380
gaagttccac aggctaaagc ccagatgccc accatagaac gagcaacctt gacaagagat    1440
ttctacctct ttcctggcaa ttga                                          1464
```

<210> SEQ ID NO 10
<211> LENGTH: 233
<212> TYPE: PRT
<213> ORGANISM: Homo sapien

<400> SEQUENCE: 10

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Tyr Phe Gly Lys
65                  70                  75                  80

Leu Glu Ser Lys Leu Ser Val Ile Arg Asn Leu Asn Asp Gln Val Leu
                85                  90                  95
```

```
Phe Ile Asp Gln Gly Asn Arg Pro Leu Phe Glu Asp Met Thr Asp Ser
            100                 105                 110

Asp Cys Arg Asp Asn Ala Pro Arg Thr Ile Phe Ile Ile Ser Met Tyr
        115                 120                 125

Lys Asp Ser Gln Pro Arg Gly Met Ala Val Thr Ile Ser Val Lys Cys
    130                 135                 140

Glu Lys Ile Ser Thr Leu Ser Cys Glu Asn Lys Ile Ile Ser Phe Lys
145                 150                 155                 160

Glu Met Asn Pro Pro Asp Asn Ile Lys Asp Thr Lys Ser Asp Ile Ile
                165                 170                 175

Phe Phe Gln Arg Ser Val Pro Gly His Asp Asn Lys Met Gln Phe Glu
            180                 185                 190

Ser Ser Ser Tyr Glu Gly Tyr Phe Leu Ala Cys Glu Lys Glu Arg Asp
        195                 200                 205

Leu Phe Lys Leu Ile Leu Lys Lys Glu Asp Glu Leu Gly Asp Arg Ser
    210                 215                 220

Ile Met Phe Thr Val Gln Asn Glu Asp
225                 230
```

<210> SEQ ID NO 11
<211> LENGTH: 702
<212> TYPE: DNA
<213> ORGANISM: Homo sapien

<400> SEQUENCE: 11

```
atgcagatct tcgtcaagac gttaaccggt aaaaccataa ctctagaagt tgaatcttcc     60
gataccatcg acaacgttaa gtcgaaaatt caagacaagg aaggcattcc acctgatcaa    120
caaagattga tctttgccgg taagcagctc gaagacggta gaacgctgtc tgattacaac    180
attcagaagg agtcgacctt acatcttgtc ttaagactaa gaggagggta ctttggcaag    240
cttgagagca aactatcggt cattcgtaat ttaaatgacc aggtcctatt tatcgaccaa    300
gggaatcgtc cactattcga ggacatgaca gacagtgact gccgagacaa tgcgccgcga    360
accattttca ttatatctat gtacaaggat tctcagccgc gcggaatggc cgtaactatt    420
tctgtcaaat gtgaaaagat atccacgctg tcgtgtgaga acaagattat tagtttcaaa    480
gagatgaatc cgccggataa tatcaaggac acgaagtctg atatcatatt tttccagcgc    540
agcgtgccgg ggcacgataa caagatgcaa tttgaatcat ccagctatga agggtacttt    600
cttgcatgcg agaaggaacg cgatctcttt aaacttattt taaagaaaga ggacgagcta    660
ggcgatcgca gcattatgtt cactgtccaa atgaagact ag                         702
```

<210> SEQ ID NO 12
<211> LENGTH: 3419
<212> TYPE: DNA
<213> ORGANISM: Homo sapien

<400> SEQUENCE: 12

```
agatctcgat cccgcgaaat taatacgact cactataggg gaattgtgag cggataacaa     60
ttcccctcta gaccacacct aaggaggat ataacatatg cagatcttcg tcaagacgtt    120
aaccggtaaa accataactc tagaagttga atcttccgat accatcgaca acgttaagtc    180
gaaaattcaa gacaaggaag gcattccacc tgatcaacaa agattgatct ttgccggtaa    240
gcagctcgag gacggtagaa cgctgtctga ttacaacatt cagaaggagt cgaccttaca    300
tcttgtctta agactaagag gagggtactt tggcaagctt gagagcaaac tatcggtcat    360
```

```
tcgtaattta aatgaccagg tcctatttat cgaccaaggg aatcgtccac tattcgagga      420
catgacagac agtgactgcc gagacaatgc gccgcgaacc attttcatta tatctatgta      480
caaggattct cagccgcgcg gaatggccgt aactatttct gtcaaatgtg aaaagatatc      540
cacgctgtcg tgtgagaaca agattattag tttcaaagag atgaatccgc cggataatat      600
caaggacacg aagtctgata tcatattttt ccagcgcagc gtgccggggc acgataacaa      660
gatgcaattt gaatcatcca gctatgaagg gtacttcctt gcatgcgaga aggaacgcga      720
tctctttaaa cttatttaa agaaagagga cgagctaggc gatcgcagca ttatgttcac        780
tgtccaaaat gaagactagt ggaggatata ataccaggaa taaataaaat ccatgggcca      840
tcatcatcat catcatggca tggatgaaag caagataaac agttattac aattttatt         900 tggttcccga caggattttt tgagaaattt taaaacttgg agtaacaaca ataacaatct      960
atcgatttat ttattaattt ttggcatagt agtattttt tataaaaaac cagaccatct       1020
aaactacatt gttgagagcg ttagtgaaat gacaacaaac ttcagaaata ataatagcct     1080
tagccgttgg ttgcccagaa gtaagtttac ccacttagac gaagagatct tgaaaagagg     1140
tggtttcatt gctggtttag ttaatgatgg taacacttgt tttatgaact ctgttttgca     1200
atcattggca tcatccagag aattaatgga gttcttggac aataatgtca taaggaccta     1260
tgaggagata aacaaaatg aacacaatga agaaggaaac gggcaagaat ctgctcaaga      1320
tgaagccact cataagaaaa acactcgtaa gggtggcaaa gtttatggta agcataagaa     1380
gaaattgaat aggaagtcaa gttcgaaaga agacgaagaa aagagccagg agccagatat     1440
cactttcagt gtcgccttaa gggatctact ttctgcctta aatgcgaagt attatcggga     1500
taaaccctat ttcaaaacca atagtttatt gaaagcaatg tccaaatctc aagaaaaaa     1560 tattcttctt ggctacgacc aagaggacgc gcaagaattc ttccagaaca tactagccga     1620
gttggaaagt aacgttaaat cattgaatac tgaaaaacta gataccactc cagttgcgaa     1680
atcagaatta cccgatgatg ctttagtagg tcaacttaac cttggtgaag ttggcactgt     1740
ttacattcca actgaacaga ttgatcctaa ctctatacta catgacaagt ccattcaaaa     1800
tttcacacct ttcaaactaa tgactccttt agatggtatc acggcagaaa gaattggttg     1860
tttacagtgt ggtgagaacg gtggcataag atattccgta ttttcgggat taagcttaaa     1920
tttaccgaac gagaatattg gttccacttt aaaattatct cagttattga gcgactggag     1980
taaacctgaa atcatcgaag tcgtagaatg taaccgttgt gccctcacag cagcgcactc     2040
tcatttattt ggtcagttga aagaatttga aaaaaaacct gagggttcga tcccagaaaa     2100
gccaattaac gctgtaaaag atagggtcca tcaaatcgaa gaagttcttg ccaaaccagt     2160
tattgacgat gaagattata agaagttgca tacagcaaat atggtacgta aatgctctaa     2220
atctaagcag atttaatat caagacctcc accattatta tccattcata tcaacagatc       2280
cgtatttgat ccaagaacgt acatgattag aaaaaataac tcgaaagtat tgtttaagtc     2340
aacgttgaat cttgcccctt ggtgttgtga tattaatgaa atcaatttgg atgctcgttt     2400
gccaatgtca aaaaggaaa aagctgcgca acaagattca agtgaagatg aaaacattgg     2460
cggtgaatac tatacgaaat tacatgaacg cttcgagcag gaatttgaag acagcgagga     2520
agaaaaagaa tacgatgacg cagaggggaa ctatgcgtct cattcaaatc ataccaagga     2580
tatcagtaac tatgatcccc taaacggtga agtcgatggc gtgacatccg atgatgaaga     2640
tgagtacatt gaagaaaccg atgctttagg gaatacaatc aaaaaaagga tcatagaaca     2700
ttctgatgtt gaaaacgaga atgtaaaaga taatgaagaa ctgcaagaaa tcgacaatgt     2760
```

-continued

```
gagccttgac gaaccaaaga tcaatgttga agatcaacta gaaacatcat ctgatgagga    2820
agatgttata ccagctccac ctatcaatta tgctaggtca ttttccacag ttccagccac    2880
tccattgaca tattcattgc gctctgtcat tgttcactac ggtacccata attatggtca    2940
ttacattgca tttagaaaat acaggggttg ttggtggaga atatctgatg agactgtgta    3000
cgttgtggac gaagctgaag tcctttcaac acccggtgta tttatgttat tttacgaata    3060
tgactttgat gaagaaactg ggaagatgaa ggatgatttg gaagctattc agagtaataa    3120
tgaagaagat gatgaaaaag agcaggagca aaaaggagtc caggagccaa aggaaagcca    3180
agagcaagga gaaggtgaag agcaagagga aggtcaagag cagatgaagt tcgagagaac    3240
agaagaccat agagatattt ctggtaaaga tgtaaactaa gctcgagcac caccaccacc    3300
accactgaga tccggctgct aacaaagccc gaaaggaagc tgagttggct gctgccaccg    3360
ctgagcaata actagcataa ccccttgggg cctctaaacg ggtcttgagg ggtttttttg    3419
```

METHOD FOR PREPARING A PHYSIOLOGICALLY ACTIVE IL-18 POLYPEPTIDE

CROSS REFERENCE TO PRIOR APPLICATIONS

This application is a divisional of U.S. application Ser. No. 10/311,491 (which is now issued as U.S. Pat. No. 7,186,528), filed 16 Dec. 2002, which is a 371 of International Application No. PCT/US01/18804, filed 11 Jun. 2001, which claims the benefit of U.S. provisional Application 60/211,832, filed 15 Jun. 2000, and claims the benefit of U.S. provisional Application 60/224,128, filed 10 Aug. 2000, and claims the benefit of U.S. provisional Application 60/264,923, filed 30 Jan. 2001.

BACKGROUND OF THE INVENTION

The present invention relates to a process for producing a physiologically active polypeptide, more particularly, to a process for producing active human IL-18.

IL-18, also known as interferon-γ-inducing factor, is a recently discovered novel cytokine. Active IL-18 contains 157 amino acid residues. It has potent biological activities, including induction of interferon-γ-production by T cells and splenocytes, enhancement of the killing activity of NK cells and promotion of the differentiation of naïve $CD4^+$ T cells into Th1 cells. In addition, human IL-18 augments the production of GM-CSF and decreases the production of IL-10. IL-18 has been shown to have greater interferon-γinducing capabilities than IL-12 and signals through a different receptor and utilizes a distinct signal transduction pathway.

IL-18, the encoding nucleotide sequence, and certain physicochemical chemical properties of the purified protein is known (Ushio, S., et al., 1996, J. Immunology, 156, 4274-4279; Dinarello, C. A., et al. 1998, J. Leukocyte Biology, 1998. 63, 658-664).

Kabushiki Kaisha Hayashibara Seibutsu Kayaku Kenkyujo's ("Hayashibara"), U.S. Pat. No. 5,912,324, which corresponds to EP 0692536, published on Jan. 17, 1996, discloses a mouse protein which induces IFN-gamma production by immunocompetent cells, the protein being further characterized as having certain physicochemical properties and a defined partial amino acid sequence. Also disclosed is a protein having a 157 aa sequence, two fragments thereof, DNA (471 bp) encoding the protein, hybridomas, protein purification methods, and methods for detecting the protein.

Hayashibara's U.S. Pat. No. 6,214,584, which corresponds to EP 0712931, published on May 22, 1996, discloses a 157 aa human protein and homologues thereof, DNA encoding the protein, transformants, processes for preparing the protein, monoclonal antibodies against the protein, hybridomas, protein purification methods, methods for detecting the protein, and methods of treatment and/or prevention of malignant tumors, viral diseases, bacterial infectious diseases, and immune diseases.

Incyte Pharmaceuticals, Inc.'s, WO 97/24441, published on Jul. 10, 1997, discloses a 193 amino acid protein corresponding to IL-18 precursor and encoding DNA.

In human cells, polypeptides formed by the expression of genes may be processed by intracellular enzymes to be partially digested and to receive sugar chains. Polypeptides to be satisfactorily incorporated into pharmaceuticals may be those which were processed similarly as in human cells. It is known that most cytokines are usually produced as precursors with no biological activity, and then processed by intracellular enzymes to be converted into active polypeptides.

The IL-18 polypeptide usually exists in human cells in the form of a precursor of 193 amino acids and no biological activity. The precursor IL-18 is also referred to as Pro-IL-18. One method of producing active IL-18 from its precursor is taught by Hayashibara's U.S. Pat. No. 5,879,942, which corresponds to EP 0819757, published on Jan. 21, 1998. The patent discloses an enzyme or a protein which converts a precursor of IL-18 into active IL-18.

Another method of producing active IL-18 from its precursor is taught by Hayashibara's U.S. Pat. No. 5,891,663, which corresponds to EP 0821005, published on Jan. 28, 1998. The patent discloses contacting precursor IL-18 with interleukin-1β-converting enzyme ("ICE"). The teachings of the patents and references are incorporated by reference.

The role of ICE as a mediator of apoptosis and inflammation has been extensively studied in the literature. It is also known that ICE can process precursors of both Interleukin-1 and Interleukin-18 to active forms (Thornberry, N A, et al., 1992, Nature 356, 768-774; Ghayur, T et al., 1997, Nature 386, 619-623).

SUMMARY OF THE INVENTION

The present invention provides methods for the in vitro activation of precursor of human IL-18 (also known as Pro-IL-18) with an activating enzyme comprising, contacting the precursor human IL-18 with an activating enzyme, such as caspase 4 or caspase 5. More specifically, the present invention provides a method by which caspase 4 and caspase 5 act on a precursor of IL-18 to cleave a specific site to produce an active polypeptide that induces IFN-γ production in immunocompetent cells.

The present invention further provides methods for the in vivo activation of precursor of human IL-18 comprising co-expressing the protein with an activating protease. More specifically, the present invention provides methods for the in vivo activation of IL-18 using proteases such as, caspase 4, also known as $ICE_{REL}II$, caspase 5, also known as $ICE_{REL}III$, and ubiquitin-specific protease, which act on a precursor of the IL-18 polypeptide to convert it into an active polypeptide that induces IFN-γ production.

BRIEF DESCRIPTION OF THE ACCOMPANYING DRAWINGS

FIG. 1 is a schematic diagram of a bicistronic expression cassette contained within pET28-ProIL-18/Casp 4 for co-expressing of Pro-IL-18 and truncated caspase 4 in E. coli.

FIG. 3 is a schematic diagram of bicistronic expression cassette contained within pET28-Pro-IL18/truncated caspase-5 for co-expression of Pro-IL8 and Caspase-5 in E. coli.

FIG. 6 shows IL-18 activity assay using KG-1 (human myelomonocytic cell line) cells and to monitor IFN-γproduction (IL-18 expressed in various ways as indicated).

FIG. 7 shows IL-18 activity assay using purified human PBMCs to monitor IFN-γproduction (IL-18 expressed in various ways as indicated).

FIG. 8 is a schematic diagram of a bicistronic expression cassette contained within pET28-ProIL-18/Casp 4 for co-expressing of Pro-IL-18 and truncated caspase 4 in E. coli.

FIG. 9 shows a sequence of Pro-IL-18/Caspase 4 expression cassette within pET28 (SEQ ID NO:8).

FIG. 10 shows the annotated sequence of Pro-IL-18/Caspase 4 expression cassette. Numbering corresponds to the position within the pET28a vector.

FIG. 11 shows Pro-IL-18/Caspase 4 induction.

FIG. 12 is a Schematic diagram of bicistronic expression cassette contained within pET28-Pro-IL18/truncated caspase-5 for co-expression of Pro-IL8 and Caspase-5 in *E. coli*.

FIG. 13 shows a sequence of Pro-IL-18/Caspase 5 expression cassette within pET28 (SEQ ID NO:9).

FIG. 14 shows the annotated sequence diagram of Pro-IL-18/truncated caspase-5 expression cassette detailing regulatory sequence features and translation of Pro-IL-18 and truncated caspase-5. Numbering corresponds to the positioning within the pET28a vector FIG. 15 shows Pro-IL-18/Caspase 5 induction.

FIG. 16 shows the amino acid sequence of Ub-IL-18 (SEQ ID NO: 10).

FIG. 17 shows the nucleic acid sequence encoding the amino acid sequence of Ub-IL-18 (SEQ ID NO: 11).

FIG. 18 shows the nucleic acid sequence of Ub-IL-18/Ubp-1 expression cassette within the pET28 vector (SEQ ID NO: 12).

FIG. 19 shows the annotated sequence of Ub-IL-18/Ubp-1 within the pET28 vector. Numbering corresponds to the position within pET28.

FIG. 20 shows Ub-IL-18 expression and processing by Ubp-1.

FIG. 21 shows IL-18 activity assay using KG-1 (human myelomonocytic cell line) cells and to monitor IFN-γ production (IL-18 expressed in various ways as indicated).

FIG. 22 shows IL-18 activity assay using purified human PBMCs to monitor IFN-γ production (IL-18 expressed in various ways as indicated).

DETAILED DESCRIPTION OF THE INVENTION

Figure 2:
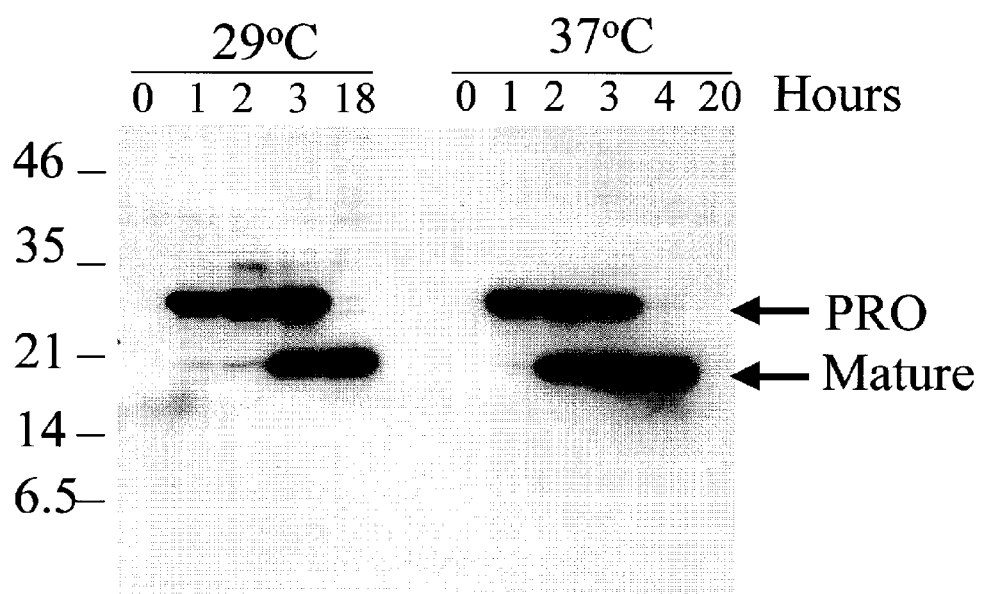
FIG. 2 shows Pro-IL-18/Caspase 4 induction.

Caspase 4 and 5 are members of a family of cysteine proteases that include Interleukin-1β converting enzyme (ICE), which preferentially cleave substrates containing a protease activation motif comprising the amino acid sequences XEYD, wherein X is selected from a group of amino acids consisting of W, L, F, Y, I, V, D, or E ; E is glutamic acid; Y is selected from a group of amino acids consisting of H, I, A, T, S, P or E; and D is aspartic acid (Munday, N. A., et al., 1995, J. Biol. Chemistry, 270, 15870-15876; Talanian, R. V. et al, 1997, J. Biol. Chemistry 272, 9677-82; Thornberry, N. A. et al. 1997 J. Biol. Chemistry 272, 17907-11). The substrate recognition of caspase-5 is thought to be essentially the same for ICE and caspase4 and distinct from other members of the caspase (Talanian, R. V. et al, 1997, J. Biol. Chemistry 272, 9677-82; Thornberry, N. A. et al. 1997 J. Biol. Chemistry 272, 17907-11). Caspase 4 is disclosed in EP-B-0 754 234. Caspase 5 is disclosed in U.S. Pat. Nos. 5,552,536 and 5,760,180.

Ubiquitin-specific proteases are a family of ATP-independent enzymes that can precisely cleave the evolutionarily conserved 76 amino acid ubiquitin peptide from the N-terminus of proteins that are fused to it. These proteases specifically cleave the peptide bond between the carboxyl-terminal amino acid residue of a ubiquitin protein and the α-amino group of any non-ubiquitin protein to which ubiquitin is joined. Ubiquitin-specific proteases from *Saccharomyces cerevisiae*, Ubp1, Ubp-2, and Ubp-3, for example, are known and can be recombinantly expressed to catalyze deubiquitination reactions that target ubiquitin fusion proteins both in vivo and in vitro (Baker, R T et al., 1992, J. Biol. Chem. 267: 23364-23375; Baker, R T et al., 1994 J. Biol. Chem. 269: 25381-25386). The specificity of *Saccharomyces cerevisiae* ubiquitin-specific proteases allows for the precise removal of ubiquitin from any peptide with the exception of those that start with proline. Ubiquitin-specific protease from other species such as mouse Unp and its human homologue Unph, are capable of efficient cleavage even in front of proline (Gilchrist C A et al. 1997, J. Biol. Chem. 272:32280-32285. Thus, virtually any desired N-terminus can be generated through the removal of a precisely fused ubiquitin peptide when combined in vitro or co-expressed with ubiquitin-specific proteases. Ubiquitin specific proteases are disclosed in U.S. Pat. Nos. 5,212,058; 5,683,904; 5,391,490; and 5,494,818.

Any natural and artificially produced caspase 4, caspase 5, or ubiquitin protease can be used in the present invention as long as they produce active polypeptides that induce IFN-γ production in immunocompetent cells independently of their structures, sources and origins.

In human cells, polypeptides formed by the expression of genes may be processed by intracellular enzymes. Intracellular enzymes cleave the precursor proteins, such as Pro-IL-18, into their active form. Polypeptides to be satisfactorily incorporated into pharmaceuticals should receive processing similar to the processing polypeptides receive in human cells. The polypeptides usually exist in human cells in the form of a precursor and no biological activity. It is known that most cytokines, including the IL-18 polypeptide, are usually produced as precursors with no biological activity, and then processed by intracellular enzymes to be converted into active polypeptides.

The precursor of IL-18 as referred to in the present invention exists, for example, in cells which inherently produce the polypeptide, in mammalian host cells, and in a bacterial system, such as *E. coli*, transformed by introducing a DNA, e.g., a DNA with the nucleotide sequence of SEQ ID NO:2, containing a region which encodes the polypeptide. Using such mammalian and bacterial host cells, precursor IL-18 can be co-expressed with proteases to generate active IL-18.

In Vitro Cleavage

The present invention provides methods for the in vitro activation of a precursor polypeptide, such as the precursor of IL-18 comprising, contacting the precursor polypeptide with an activating enzyme.

In a preferred embodiment, the present invention provides a method for the in vitro activation of precursor of human IL-18 comprising, contacting the precursor human IL-18 with caspase 4 or caspase 5.

In a preferred embodiment, the precursor of IL-18 is activated in vitro by cleaving with the activating enzyme which recognizes a specific protease activation motif comprising the amino acid sequence XEYD, wherein X is selected from a group of amino acids consisting of W, L, F, Y, I, V, D or E ; and Y is selected from a group of amino acids consisting of H, I, A, T, S, P or E.

In a further preferred embodiment, the precursor of IL-18 is activated in vitro by cleaving the peptide linkage between the aspartic acid 36 and tyrosine 37 in SEQ ID NO: 1 with caspase 4 or caspase 5 to produce an active polypeptide that induces IFN-γ production in immunocompetent cells.

Generally, caspase 4 or caspase 5 can be obtained from cells, which inherently produce it, and transformants obtained by applying recombinant DNA technology. Examples of such cells are those which were established from mammal and human cells such as epithelial cells, endothelial cells, interstitial cells, cartilage cells, monocytes, granulocytes, lymphocytes, and established cell lines thereof. Examples of the transformants include transformed microorganisms and animal cells obtained by introducing a DNA encoding caspase 5 into microorganisms and animal cells. Caspase 4 or caspase 5 is prepared by culturing these transformants in conventional culture media used in this field, either treating them with ultrasonics in the form of intact cultures or after separated from the cultures or soaking the transformants in hypotonic solvents, applying to the resulting cell debris or mixtures containing culture supernatants and cell debris the following conventional techniques used for purifying enzymes in this field; salting out, dialysis, filtration, concentration, separatory sedimentation, ion-exchange chromatography, gel filtration chromatography, adsorption chromatography, isoelectric chromatography, hydrophobic chromatography, reverse-phase chromatography, affinity chromatography gel electrophoresis and electrofocusing. Two or more of these purification methods can be used in combination. The DNA encoding caspase 4 and caspase 5 and transformants which produce caspase 4 and caspase 5 are known in the art. For example, the enzymes may be produced in active form in *E. coli* by expression of N-terminally truncated peptides lacking the pro region, as described (Munday N A et al., 1996, J. Biol. Chem 26:15870-76.)

Cells which produce the precursor polypeptide, such as Pro-IL-18, inherently or those which were transformed to produce the precursor are cultured in nutrient culture media. Preferred culture media include culture media well known in the art, such as Luria-Bertani medium or other rich medium for culturing *E. coli* comprising tryptone and yeast extract.

Caspase 4 or caspase 5, obtained using the above method, is allowed to coexist in the resulting cultures or added to the resulting mixtures or cell debris after disrupting the proliferated cells separated or unseparated from the cultures. The amount of caspase 4 or caspase 5 required is less than the equimolar of the precursor. The caspase 4 or caspase 5 is contacted with the precursor at temperatures and pHs, which allow the caspase 4 or caspase 5 to act on the precursor, usually, the caspase 4 or caspase 5 is allowed to react with the precursor until the desired amount of active polypeptide is formed from the material precursor at temperatures of about 4°-40° C. and pHs of about 6-9. The preferred temperature is about 25° C. and the preferred pH is about 7.2. Thus, reaction mixtures containing the active polypeptide can be obtained.

The activity of caspase 4 or caspase 5 may be assayed and expressed by units for activity according to the μg processed polypeptide produced per μg caspase 4 or caspase-5 per minute.

In Vivo Co-Expression

The present invention further provides methods for the in vivo activation of a precursor polypeptide, such as a precursor of IL-18 comprising co-expressing the protein with an activating protease. More specifically, the present invention provides methods for the in vivo activation of IL-18 comprising the bicistronic co-expression of polypeptides, such as IL-18, with proteasese such as, caspase 4, also known as $ICE_{REL}II$, caspase 5, also known as $ICE_{REL}III$, and ubiquitin.

In a preferred embodiment, human caspase 4, also known as $ICE_{REL}II$, is co-expressed bicistronically with human Pro-IL-18 to allow for the in vivo processing of Pro-IL-18 into active IL-18.

In another preferred embodiment, truncated human caspase 4 (SEQ ID NO. 4), is co-expressed bicistronically with human Pro-IL-18 to allow for the in vivo processing of Pro-IL-18 (SEQ ID NO:1) into active IL-18 (SEQ ID NO:3).

In another preferred embodiment, human caspase 5, also known as $ICE_{REL}III$, is co-expressed bicistronically with human Pro-IL-18 to allow for the in vivo processing of Pro-IL-18 into active IL-18 (SEQ ID NO:3).

In yet another preferred embodiment, ubiquitin protease 1 (Ubp-1) is co-expressed bicistronically with Ubiquitin-IL-18 (Ubp-IL-18) for the in vivo processing of Ub-IL-18 into active IL-18.

In yet another preferred embodiment, ubiquitin protease 1 (Ubp-1) is co-expressed bicistronically with Ubiquitin-IL-18 (Ubp-IL-18) for the in vivo processing of UB-IL-18 (SEQ ID NO:9) into active IL-18 (SEQ ID NO. 3).

In the most preferred embodiment, truncated human caspase 5 (SEQ ID NO. 5), is co-expressed bicistronically with human Pro-IL-18 to allow for the in vivo processing of Pro-IL-18 (SEQ ID NO:1) into active IL-18 (SEQ ID NO:3).

Figure 4:
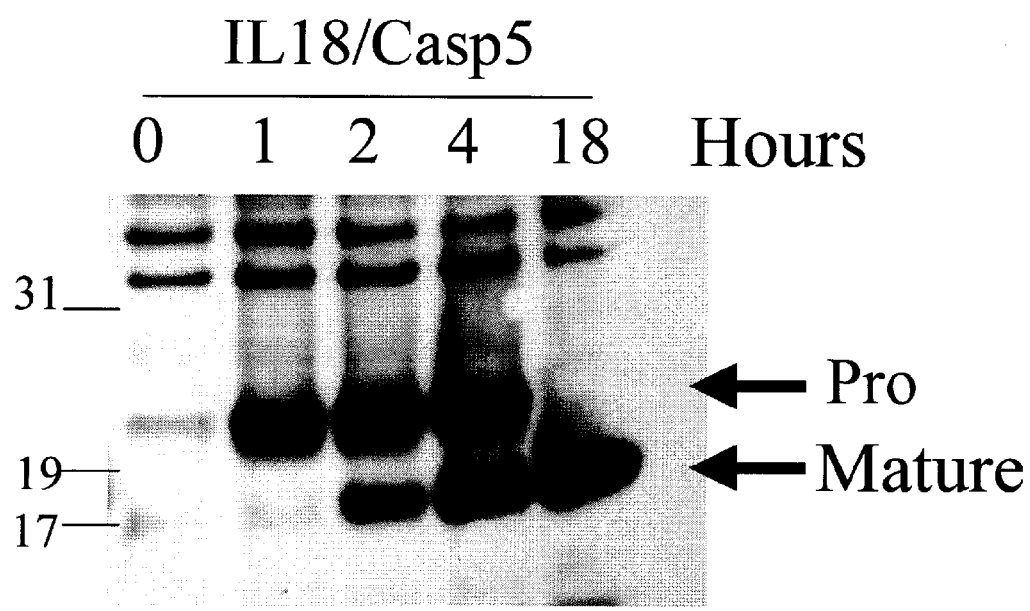
FIG. 4 shows Pro-IL-18/Caspase 5 induction.

A DNA encoding caspase 4 or caspase 5 and a DNA encoding a precursor of the polypeptide are both introduced into an appropriate bacterial or mammalian host cell to transform it. In this case, caspase 4 or caspase 5, formed by the DNA expression, acts on a precursor of the polypeptide, formed by the DNA expression in the same transformant, to form an active polypeptide (FIGS. 2 and 4). Preferred host cells are epidermal-, interstitial-, neuroblast-, hematopoietic-cell lines, which are derived from humans, monkeys, mice and hamsters and used conventionally as hosts, such as 3T3 cells including 3T3-Swiss albino cells (ATCC CCL 92), C1271 cells (ATCC CRL 1616), CHO cells including CHO-K1 cells (ATCC CCL 61), CV-1 cells (ATCC CCL 70), COS cells including COS-1 cells (ATCC CCL 1650), HeLa cells (ATCC CCL 2), MOP cells including MOP-8 cells (ATCC CRL 1709) and mutants thereof. Most preferred host cells are *E. coli*. The most preferred method is of introducing DNA encoding caspase 4 or 5 and a DNA encoding a precursor of the polypeptide into *E. coli* is chemical transformation with rubidium chloride, which is well known in the art. Methods to introduce a DNA encoding caspase 4 or caspase 5 and a DNA encoding a precursor of the polypeptide into mammalian host cells include conventional DEAE-dextran method, phosphoric acid-calcium method, electroporation, lipofection, microinjection, and virus-infection method using retrovirus, Adenovirus, herpesvirus and vaccinia virus. In this case, vectors such as pCD, pcDL-SRα, pKY4, pCDM8, pCEV4, pME18S and pSV2-gpt, including appropriate promoters, enhancers, replication origins, termination sites, splicing sequences, polyadenylation sequences and/or selection markers can be used following standard techniques described in Ausubel F M et al., 1994 Current Protocols in Molecular Biology, New York: Greene Publishing Assoc. and Wiley Interscience. Clones, which were observed by immunological detection to produce an activated polypeptide, were selected by choosing the desired clone from transformants after culturing in nutrient culture media. Cultures containing the active polypeptide can be obtained by culturing the cloned transformant with conventional nutrient culture used in this field. As for cells which inherently produce a precursor of the polypeptide and other cells which were transformed to produce the polypeptide, they may produce the precursor along with activating enzymes, which activate the polypeptide, such as caspase 4, caspase 5, and ubiquitin. Recombinant DNA technologies using mammalian host cells are disclosed in detail in Glutzman, Cell, 23:175 (1981) Mullingan, PNAS 78:2072 (1981). Recombinant DNA technologies using bacterial host cells are described in Protein Expression: A Practical Approach, S. J. Higgins and B. D. Hames eds. 1999, New York, Oxford University Press.

While the resulting reaction mixtures and cultures containing an active IL-18 polypeptide can be used intact as an IFN-γ inducer, in a preferred embodiment, cells in the cultures are disrupted by ultrasonics, cell lysis enzymes and/or surfactants, followed by separating the polypeptide from the resulting cells and cell debris by filtration, centrifugation, etc., following standard industry procedures described in Protein Purification:Principles and Practice, Cantor, C. R. ed. 1993, New York, Spinger-Verlag. The polypeptide free of cells and cell debris may be purified by conventional purification methods used to purify biologically active substances in this field, for example, salting out, dialysis, filtration, concentration, separatory sedimentation, ion-exchange chromatography, gel filtration chromatography, adsorption chromatography, isoelectric chromatography, hydrophobic chromatography, reverse-phase chromatography, affinity chromatography, gel electrophoresis and electrofocusing. If necessary, two or more of these purification methods can be used in combination. The resulting purified polypeptide can be concentrated and lyophilized into a liquid or solid product to meet their final uses.

The bicistronic expression cassettes of the present invention are versatile vectors which can be used for the in vivo processing of virtually any peptide containing the appropriate caspase 4/caspase 5 or ubiquitinase cleavage recognition sites as have been previously described (Tobias, J. W. et al., *Journal of Biological Chemistry*, 1991. 266(18): p. 12021.12028; Talanian, R. V. et al., *Journal of Biological Chemistry*, 1997. 272(15): p. 9677-9682). Bicistronic expression offers advantages over other co-expression strategies because both genes are tied to the same transcription unit, ensuring consistent expression of both genes over time. This is in contrast to dual plasmid systems where one plasmid can be lost over time, or single plasmid dual promoter systems where expression may vary from each promoter from one experiment to the next. In particular, the bicistronic expression systems described here are ideally suited for the in vivo activation of enzymes, cytokines, growth factors, and other proteolytically activatable proteins, thereby enabling large-scale production of such proteins from cells in a single step and eliminating the need for a separate in vitro activation step.

Activating proteases, truncated caspase 4 (Ala105 to Asn377) or truncated caspase 5 (Ile146 to Asn418), were subcloned as N-terminal 6-His fusions immediately following the Pro-IL-18 sequence in order to generate a transcriptional fusion of the two genes. A T7 terminator sequence is located downstream of the caspase4 sequence for translational termination of the bicistronic transcription unit. A small intergenic region including a defective Shine-Dalgarno sequence was also added to permit only minimal translation initiation from the caspase4 sequence. Other regulatory regions include a 25 basepair lac operator sequence located immediately downstream of the 17 basepair promoter region which is bound by lac repressor encoded by a copy of the lac-I gene located on the plasmid, thereby suppressing basal transcription in the absence of T7 RNA polymerase. The resultant plasmids designated ProIL18/Casp4 and ProIL18/Casp5 were then separately transfected into *E. coli* BL21 (DE3) strain that contains an inducible chromosomal copy of the T7 polymerase gene.

The transcription of the bicistronic cassette is under the direction of the T7 promoter, which is controlled by the phage T7 RNA polymerase protein, encoded from a lysogenic copy of the T7 RNA polymerase gene. This chromosomal copy of T7 polymerase is itself under lacUV5 promoter control, inducible by the addition of isopropyl-1-thio-b-D-galactopyranoside. Induction leads to the coordinate transcription and translation of Pro-IL-18 and His-caspase4 or His-caspase-5. Nascently translated caspase4 or caspase-5 is autoprocessed to an active species, which initiates the proteolytic activation ProIL-18. Both the translated precursor IL-18 as well as the post-translationally activated IL-18 are mainly soluble inside *E. coli*. Mature active IL-18 containing an N-terminal tyrosine is purified directly from bacterial cell lysates following induction by conventional chromatography methods. Cleavage to mature IL-18 with caspase4 is complete by 4 hours at 37° C. or by 18 hours at 29° C. (FIG. 2) and cleavage to mature IL-18 with caspase-5 is complete by 18 hours at 29° C. (FIG. 4).

In the most preferred embodiment, the present invention uses a truncated caspase 4, as shown in (SEQ ID NO:4 and SEQ ID NO:5), or truncated caspase 5 (SEQ ID NO: 6 and SEQ ID NO: 7). Truncation of caspase 4 and caspase 5 is disclosed in Munday, N. A., et al., 1995, J. Biol. Chemistry, 270, 15870-15876.

Figure 5:
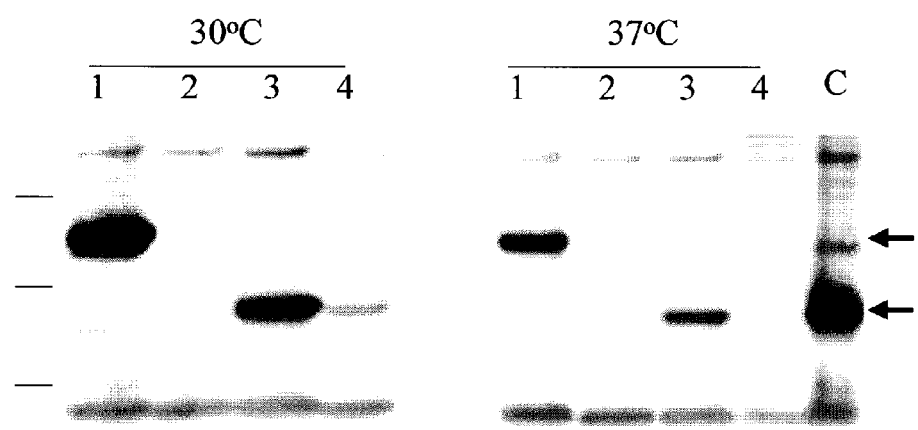
FIG. 5 shows Ub-IL-18 expression and processing by Ubp-1.

The present invention further provides a method for creating an active polypeptide by co-expression of a ubiquitin-specific protease with an N-terminal ubiquitin IL-18 fusion (precursor) which is converted to active IL-18 by the ubiquitin c-terminal hydrolase activity. A 76 amino acid ubiquitin protein containing an authentic N-terminal tyrosine is fused to the mature N-terminus of human IL-18 and coexpressed with a ubiquitin-specific protease in *E. coli* for example as shown in SEQ ID NO:10 and SEQ ID NO: 11. Ubiquitin is a highly conserved 76-residue protein found in eucaryotic cells that function to mark proteins for degradation (Baker, R. T., Current Opinion in Biotechnology, 1996. 7(5): p. 541-6). Ubiquitin is specifically cleaved from protiens by the action of ubiquitin-specific proteases that are endogenously expressed in eucaryotic cells but which are absent in bacteria. The co-expression of ubiquitin fused proteins with ubiquitin-specific proteaese in *E. coli* also leads to the efficient removal of ubiquitin (Baker, R. T. et al., Journal of Biological Chemistry, 1992. 267(32): p. 23364-75) (FIG. 5). In addition, most of these deubiquitinating enzymes are capable of cleaving in front of virtually any amino acid with the exception of proline. Thus, cleavage of ubiquitin from mature IL-18 is possible despite the presence of the large aromatic tyrosine residue in the P1' position.

The co-expression of Ubiquitin-IL-18 (Ub-IL-18) and Ubiquitin protease-1(Ubp-1) (Tobias, J. W. et al., *Journal of Biological Chemistry*, 1991. 266(18): p. 12021.12028) is accomplished through the bicistronic expression of the two genes under inducible T7 promoter control. Mature IL-18 is expressed as an N-terminal fusion with the evolutionarily conserved 76 amino acid ubiquitin peptide. The Ub-IL-18 cDNA is subcloned under the control of the T7 RNA polymerase promoter within pET28a vector. Subsequently, the cDNA encoding full-length ubiquitin-specific protease is subcloned downstream preceding the T7 terminator sequence (FIG. 19). Both Ub-IL-18 and Ubiquitin-specific protease cDNAs are transcribed into a single mRNA transcript from which Ub-IL-18 and Ubiquitin-specific protease proteins are separately translated.

As described above, the active human IL-18 polypeptide, obtained by the present methods has an activity of inducing the production of IFN-γ as a useful biologically active substance, stimulates the production of IENg from KG-1 (human myelomonocytic cell line) cells (FIG. 6) and purified human PBMCs (FIG. 7).

All publications and patents are hereby incorporated by reference. The following examples further explain but do not limit the present invention:

EXAMPLE 1

Preparation of precursor IL-18 (pro-IL-18)

Human-precursor IL-18 was expressed as an N-terminal hexa-histidine tagged fusion in E. coli. The expression plasmid, ProEx-hIL18, was derived from a vector, pPROEX-1 (Life Technologies) containing the Trc promoter and Iaclq for inducible expression with isopropyl-1-thio-β-D-galactopyranoside (IPTG). In order to construct the recombinant expression vector, a DNA fragment containing the entire caspase 5 precursor gene was PCR amplified from a cDNA clone, tailing 5' with Nde I and 3' with Bam HI restriction endonuclease sites. The amplified product was subcloned between these two restriction sites in pPROEX-, thus generating an in frame N-terminal fusion with the hexa-histidine coding sequence present in the vector.

The resultant plasmid was expressed in DH10B host cells following induction with 1 mM IPTG for 5 hours at 37° C. Recombinant protein was harvested from cell pellets obtained following centrifugation of the induced cultures.

EXAMPLE 2

Purification of pro-IL-18

1.5 kg of E coli cells expressing pro-IL-18 as described in EXAMPLE 1 was suspended in 3.6 L lysis Buffer C (50 mM Tris HCl, 10 mM BME, 0.5 M NaCl, 5% glycerol, 1 ug/ml pepstatin A, 1 ug/ml leupepsin, 0.4 mM AEBSF), lysed by two passes through Microfluidics at 12,000 psi, centrifuged at 28,000×g, and 3.7 L supernatant were collected. 600 ml of NiNTA agarose preequilibrated with Buffer C containing 5 mM imidazole (Buffer D) was added to the supernatant and incubated the slurry for one hour to capture pro-IL-18. The slurry was centrifuged at low speed (3,000 rpm), the supernatant was decanted, and the slurry was packed in a column. The column was washed with Buffer D and pro-IL-18 was eluted with 300 mM imidazole in Buffer C. The pool was dialyzed in Buffer E (25 mM HEPES, 10 mM BME, pH 8.0) and applied to DEAE ToyoPearl 650M column equilibrated with the same buffer. The column was eluted with a linear gradient of 0 to 0.5 M NaCl in Buffer E. The pool contained 650 mg of >90 % pure pro-IL-18.

EXAMPLE 3

Preparation of Caspase 4

Human caspase-4 was also expressed as an N-terminal Hexa-histindine tagged fusion in E. coli. The expression plasmid, pET16b-caspase 4, was derived from a vector pET16b (Novagen) containing the phage T7 promoter. The recombinant vector was constructed by PCR amplification of the caspase-4 active domain (amino acids Ala105 to Asn377) incorporating a hexa-histidine coding sequence at the N-terminus and tailing with Nco I and Xho I restriction endonuclease sites. The resultant PCR product was then subcloned between these two restriction sites to generate the N-terminal Hexa Histidine-Caspase 4 fusion vector.

The resultant plasmid was transformed into the lysogenic BL21 DE3 E. coli strain containing a chromosomal copy of T7 RNA polymerase under lacUV5 promoter control enabling inducible expression of caspase 4 following induction with 1 mM IPTG. Active protein was purified from cell pellets isolated following induction at 37° C. for 3 hours.

EXAMPLE 4

Purification of Caspase 4

When E. coli cells expressing N-terminal hexa-His tagged human caspase 4 described in Example 2 are lysed, caspase 4 activity can be detected in the lysate supernatant. When the protein is captured on NiNTA agarose beads from the supernatant, both p10 and p20 are recovered. This indicates that caspase 4 protease domain is activated during cell culture through autocleavage at the junction of p10 and p20 and remains as a soluble noncovalent heterodimer. With this information, hexa-His tagged p20/p10 heterodimer can be purified. The entire process is carried out at 4° C. to avoid any further breakdown of the molecule.

Approximately 400 g of wet E. coli cell pellet was suspended in 1.6 L of lysis buffer containing 25 mM HEPES, 0.1% CHAPS, 500 mM NaCl, 10 mM beta mercaptoethanol (BME) at pH 7.4, and 10% glycerol (Buffer A) and lysed by two passes through Microfluidics at 12,000 psi. The lysate was centrifuged at 30,000×g for one hour and lysate supernatant, 1.7 L, was recovered. NiNTA agarose, 150 ml, which was preequilibrated with lysis buffer containing 5 mM imidazole, was added to the lysate supernatant, the suspension was adjusted to pH 8.0 with 2 N NaOH, and caspase 4 was batch-absorbed for one hour. NiNTA agarose was packed in the column, washed with 5 mM and 25 mM imidazole in Buffer A sequentially to remove impurities, and caspase 5 was eluted with 300 mM imidazole in Buffer A. The protein was dialyzed against Buffer B (25 mM HEPES, 0.1% CHAPS, 10% glycerol, 10 mM BME, pH 8.0) and applied to DEAE ToyoPearl 650M column preequilibrated with the same buffer. Caspase 4 was eluted from the column with 100 mM NaCl in the same buffer. Fractions displaying highest specific activity of caspase 4 using fluorescent peptide substrate, LEED-AMC, were pooled.

EXAMPLE 5

In Vitro Activation and Preparation of Polypeptide

Pro-IL-18 purified as described in Example 2 was incubated with truncated caspase 4 with a his tag at 1:500 w/w ratio for 3 hours at room temperature. The cleavage reaction of prodomain was completed >90 % according to SDS-PAGE analysis. To the reaction mixture, 140 ml of NiNTA agarose in Buffer D was added, incubated for one hour, and poured to sintered glass funnel to recover unbound material containing mainly mature IL-18. Small amounts of remaining pro-IL-18, prodomain, caspase 4, and other impurities were bound to NiNTA agarose. The unbound solution was adjusted to 25 mM DTT, incubated for one hour to complete reduction reaction, adjusted the pH of the solution to 6.0 by adding 2 M phosphoric acid, and concentrated to 86 ml using YM10 membrane. The concentrated sample was applied to Superdex 75 column equilibrated with 10 mM NaPhosphate pH 6.0 containing 0.1M NaCl. Pooled fractions contained 560 mg of mature IL-18.

EXAMPLE 6

In Vivo Activation and Preparation of Polypeptide

Activation of IL-18 can also be achieved in vivo through the simultaneous expression of human precursor IL-18 and caspase-4. Pro-IL-18 is co-expressed bicistronically in *E. coli* from a single transcript with human caspase4 within the expression plasmid, pET28-Pro-IL-18/Casp4. The human pro-IL-18 gene is subcloned into pET28a (Novagen) under the control of the T7 promoter including an efficient Shine-Dalgarno sequence for optimal translation initiation from the Pro-IL-18 sequence (FIG. 1). The caspase 4 gene (Ala105 to Asn377) linked to a his tag was subcloned immediately after the Pro-IL-18 sequence including a defective Shine-Dalgarno sequence, permitting minimal translation initiation from the caspase 4 sequence. A T7 terminator sequence was included for translational termination following the bicistronic transcription unit. The resultant construct was then transfected into a BL21(DE3) host containing an inducible chromosomal copy of the T7 polymerase gene. Induction of this construct in this host with 1 mM IPTG resulted in the coordinate transcription and translation of pro-IL-18 and pro-caspase 4. Nascently translated pro-caspase 4 is autoprocessed to an active species which initiates the proteolytic activation of pro-IL-18. FIG. 1 shows a time course of IL-18 activation over 18 hours at 29° C. following 1 mM IPTG induction (0-18 hours).

EXAMPLE 7

In Vivo Activation of Caspase 4

The in vivo activation of Caspase-4 is described in (Munday, N. A., et al., 1995, J. Biol. Chemistry, 270, 15870-15876). Expression of a truncated form of caspase-4 beginning at Ala 58, lacking the proregion in *E. coli*, leads to self-activation by cleavage into P10 and P20 subunits which assemble into an active enzyme heterodimer. The delay in caspase-4 activation is translated into a delay in the cleavage and activation of Pro-IL-18 to mature IL-18. This enables accumulation of the more stable Pro-IL-18 prior to its cleavage to mature IL-18 which is less stable in cells.

EXAMPLE 8

Purification of Human IL-18 Coexpressed with Caspase 4

66 g of *E. coli* cells expressing IL-18 as described in Example 6 were suspended in 130 ml of 0.1 M HEPES pH 7.5 containing 1 mM EDTA and 10 mM DTT (entire process was performed at 4° C. and in the presence of 10 mM DTT except the last step to maintain free SH) and lysed at 15,000 psi by two passes using Microfluidics. The lysate (230 ml) was centrifuged at 34,000×g for 30 min. The supernatant (200 ml) was diluted to 1 L with 25 mM HEPES pH 7.0 and flowed through two columns in tandem, ToyoPearl SP 650M and ToyoPearl DEAE 650M. Much of the impurities derived from *E. coli* cells were bound to the columns. The flow-through material was adjusted to pH 9.5 with 25 mM bistris propane, diluted to 2 L and applied to Source 15Q column equilibrated with 25 mM bistris propane HCl pH 9.5. The column was eluted with a linear gradient of 0 to 0.5 M NaCl in the same buffer. Fractions containing IL-18 were identified using Vydac C4 RP-HPLC and pooled (250 ml). The pool was concentrated to 50 ml using YM10 membrane and applied to Superdex 75 column which was preequilibrated with 10 mM NaPO4 pH 6.0 containing 1 mM EDTA and 0.15 M NaCl (no DTT for in vivo use).

EXAMPLE 9

Preparation of Truncated Caspase 5

Human truncated caspase 5 was also expressed as an N-terminal Hexa-histindine tagged fusion in *E. coli*. The expression plasmid, pET16b- truncated caspase 5, was derived from a vector pET16b (Novagen) containing the phage T7 promoter. The recombinant vector was constructed by PCR amplification of the truncated caspase 5 active domain (amino acids Ile146 to Asn418) incorporating a hexa-histidine coding sequence at the N-terminus and tailing with Nco I and Xho I restriction endonuclease sites. The resultant PCR product was then subcloned between these two restriction sites to generate the N-terminal Hexa Histidine-truncated caspase 5 fusion vector.

The resultant plasmid was transformed into the lysogenic BL21 DE3 *E. coli* strain containing a chromosomal copy of T7 RNA polymerase under lacUV5 promoter control enabling inducible expression of truncated caspase 5 following induction with 1 mM IPTG. Active protein was purified from cell pellets isolated following induction at 37° C. for 3 hours.

EXAMPLE 10

Purification of Truncated Caspase 5

When *E. coli* cells expressing N-terminal hexa-His tagged human truncated caspase 5 described in EXAMPLE 9 are lysed, truncated caspase 5 activity can be detected in the lysate supernatant. When the protein is captured on NiNTA agarose beads from the supernatant, both p10 and p20 are recovered. This indicates that truncated caspase 5 protease domain is activated during cell culture through autocleavage at the junction of p10 and p20 and remains as a soluble noncovalent heterodimer. With this information, hexa-His tagged p20/p10 heterodimer can be purified. The entire process is carried out at 4° C. to avoid any further breakdown of the molecule.

Approximately 400 g of wet *E. coli* cell pellet was suspended in 1.6 L of lysis buffer containing 25 mM HEPES, 0.1% CHAPS, 500 mM NaCl, 10 mM beta mercaptoethanol (BME) at pH 7.4, and 10% glycerol (Buffer A) and lysed by two passes through Microfluidics at 12,000 psi. The lysate was centrifuged at 30,000×g for one hour and lysate supernatant, 1.7 L, was recovered. NiNTA agarose, 150 ml, which was preequilibrated with lysis buffer containing 5 mM imidazole, was added to the lysate supernatant, the suspension was adjusted to pH 8.0 with 2 N NaOH, and caspase 5 was batch-absorbed for one hour. NiNTA agarose was packed in the column, washed with 5 mM and 25 mM imidazole in Buffer A sequentially to remove impurities, and caspase 5 was eluted with 300 mM imidazole in Buffer A. The protein was dialyzed against Buffer B (25 mM HEPES, 0.1% CHAPS, 10% glycerol, 10 mM BME, pH 8.0) and applied to DEAE ToyoPearl 650M column preequilibrated with the same buffer. The truncated caspase 5 was eluted from the column with 100 mM NaCl in the same buffer. Fractions displaying highest specific activity of truncated caspase 5 using fluorescent peptide substrate, LEED-AMC, were pooled.

EXAMPLE 11

In Vitro Activation and Preparation of Polypeptide

Pro-IL-18 prepared and purified as described in Examples 1 and 2 was incubated with truncated caspase 5 at 1:500 w/w ratio for 3 hours at room temperature. The cleavage reaction of prodomain was completed >90% according to SDS-PAGE analysis. To the reaction mixture, 140 ml of NiNTA agarose in Buffer D was added, incubated for one hour, and poured to sintered glass funnel to recover unbound material containing mainly mature IL-18. Small amounts of remaining pro-IL-18, prodomain, truncated caspase 5, and other impurities were bound to NiNTA agarose. The unbound solution was adjusted to 25 mM DTT, incubated for one hour to complete reduction reaction, adjusted the pH of the solution to 6.0 by adding 2 M phosphoric acid, and concentrated to 86 ml using YM10 membrane. The concentrated sample was applied to Superdex 75 column equilibrated with 10 mM NaPhosphate pH 6.0 containing 0.1M NaCl. Pooled fractions contained 560 mg of mature IL-18.

EXAMPLE 12

In Vivo Activation and Preparation of Polypeptide

Activation of IL-18 can also be achieved in vivo through the simultaneous expression of human precursor IL-18 and truncated caspase 5. Pro-IL-18 was co-expressed bicistronically in *E. coli* from a single transcript with human truncated caspase 5 within the expression plasmid, pET28-Pro-IL18/Casp5. The human pro-IL-18 gene is subcloned into pET28a (Novagen) under the control of the T7 promoter including an efficient Shine-Dalgarno sequence for optimal translation initiation from the Pro-IL-18 sequence. The truncated caspase 5 gene (Ile146 to Asn418) was subcloned immediately after the Pro-IL-18 sequence including a defective Shine-Dalgarno sequence, permitting minimal translation initiation from the truncated caspase 5 sequence. A T7 terminator sequence was included for translational termination following the bicistronic transcription unit. The resultant construct was then transfected into a BL21(DE3) host containing an inducible chromosomal copy of the T7 polymerase gene. Induction of this construct in this host with 1 mM IPTG resulted in the coordinate transcription and translation of pro-IL-18 and pro-caspase 5. Nascently translated pro-caspase 5 is autoprocessed to an active species which initiates the proteolytic activation of pro-IL-18.

EXAMPLE 13

Purification of Human IL-18 Coexpressed with Truncated Caspase 5

66 g of *E. coli* cells expressing IL-18 as described in Example 12 were suspended in 130 ml of 0.1 M HEPES pH 7.5 containing 1 mM EDTA and 10 mM DTT (entire process was performed at 4° C. and in the presence of 10 mM DTT except the last step to maintain free SH) and lysed at 15,000 psi by two passes using Microfluidics. The lysate (230 ml) was centrifuged at 34,000×g for 30 min. The supernatant (200 ml) was diluted to 1 L with 25 mM HEPES pH 7.0 and flowed through two columns in tandem, ToyoPearl SP 650M and ToyoPearl DEAE 650M. Much of the impurities derived from *E. coli* cells were bound to the columns. The flow-through material was adjusted to pH 9.5 with 25 mM bistris propane, diluted to 2 L and applied to Source 15Q column equilibrated with 25 mM bistris propane HCl pH 9.5. The column was eluted with a linear gradient of 0 to 0.5 M NaCl in the same buffer. Fractions containing EL-18 were identified using Vydac C4 RP-HPLC and pooled (250 ml). The pool was concentrated to 50 ml using YM10 membrane and applied to Superdex 75 column which was preequilibrated with 10 mM NaPO4 pH 6.0 containing 1 mM EDTA and 0.15 M NaCl (no DTT for in vivo use).

EXAMPLE 14

Preparation of Ubiquitin/Pro-IL-18/Ubp1

The 76 amino acid ubiquitin coding sequence is fused in frame with the start of mature human IL-18 through blunt end ligation such that the first tyrosine codon of mature IL-18 immediately follows the glycine 76 codon of ubiquitin. The gene fusion is then subcloned into a pET vector under the control of the T7 promoter including an efficient Shine-Dalgarno sequence for optimal translation initiation from the ubiquitin-IL-18 gene sequence. The full-length Ubp-1 gene is then subcloned immediately following IL-18 including a defective Shine-Dalgarno sequence for minimal translation of Ubp-1. FIG. 2 depicts the sequence of UbIL-18/Ubp-1 expression cassette within pET28. SEQ ID NO: 9 depicts the annotated sequence of UbIL-18/Ubp-1 within pET28. Numbering corresponds to the position within pET28.

EXAMPLE 15

In Vivo Activation and Preparation of IL-18

The construct of Example 14 was then transfected into a BL21(DE3) host. Induction with 1 mM IPTG resulted in the coordinate transcription and translation of Ubiquitin-IL-18 and Ubp-1. The enzymatic action of Ubp-1 led to the efficient processing of Ub-IL-18 to mature active IL-18 which can then be directly purified from *E. coli* lysates by conventional methods. FIG. 4 illustrates the time course of IL-18 expression and processing at 30° C. and 37° C. following induction with 1 mM IPTG. The top arrow indicates the portion of unprocessed UB-IL-18 in Lane 1. Bottom arrow indicates the portion of processed IL-18 in Lane 3. (Western blot detection using anti-IL-18 antisera.)

EXAMPLE 16

Purification of Human IL-18 Coexpressed with Ubiquitin 66 g of *E. coli* cells expressing IL-18 as described in Example 15 were suspended in 130 ml of 0.1 M HEPES pH 7.5 containing 1 mM EDTA and 10 mM DTT (entire process was performed at 4° C. and in the presence of 10 mM DTT except the last step to maintain free SH) and lysed at 15,000 psi by two passes using Microfluidics. The lysate (230 ml) was centrifuged at 34,000×g for 30 min. The supernatant (200 ml) was diluted to 1 L with 25 mM HEPES pH 7.0 and flowed through two columns in tandem, ToyoPearl SP 650M and ToyoPearl DEAE 650M. Much of the impurities derived from *E. coli* cells were bound to the columns. The flow-through material was adjusted to pH 9.5 with 25 mM bistris propane, diluted to 2 L and applied to Source 15Q column equilibrated with 25 mM bistris propane HCl pH 9.5. The column was eluted with a linear gradient of 0 to 0.5 M NaCl in the same buffer. Fractions containing IL-18 were identified using Vydac C4 RP-HPLC and pooled (250 ml). The pool was concentrated to 50 ml using YM10 membrane and applied to Superdex 75 column which was preequilibrated with 10 mM NaPO4 pH 6.0 containing 1 mM EDTA and 0.15 M NaCl (no DTT for in vivo use).

While there has been described what is at present considered to be the preferred embodiments of the invention, it will be understood the various modifications may be made therein, and it is intended to cover in the appended claims all such modifications as fall within the true spirit and scope of the invention.

We claim:

1. A method for producing an active human IL-18 polypeptide from a human precursor IL-18 polypeptide, comprising:
   (i) co-expressing bicistronically caspase 4, having the amino acid sequence of SEQ ID NO:4, with the human precursor IL-18 polypeptide; and
   (ii) purifying the active IL-18 polypeptide.

* * * * *